(12) United States Patent
Bani-Hashemi et al.

(10) Patent No.: US 7,046,757 B1
(45) Date of Patent: May 16, 2006

(54) X-RAY SCATTER ELIMINATION BY FREQUENCY SHIFTING

(75) Inventors: Ali Bani-Hashemi, Walnut Creek, CA (US); Wolf-Ekkehard Blanz, Danville, CA (US); Jonathan S. Maltz, Oakland, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/109,256

(22) Filed: Apr. 18, 2005

(51) Int. Cl.
*G01N 23/00* (2006.01)

(52) U.S. Cl. .............................. 378/7; 378/19; 378/154

(58) Field of Classification Search .................... 378/4, 378/7, 19, 62, 145, 147, 149, 154–159, 207; 250/370.08, 370.09
See application file for complete search history.

(56) References Cited

U.S. PATENT DOCUMENTS 6,826,256 B1 * 11/2004 Inoue .......................... 378/154

* cited by examiner

*Primary Examiner*—Edward J. Glick
*Assistant Examiner*—Courtney Thomas (57) ABSTRACT

A method for separating and filtering noise caused by X-ray scatter contaminations from the primary signal component of the signal produced by the detector assembly of a radiographic imaging device employs a scatter removal screen or grating disposed between the object being imaged and the detector assembly. The grating has an absorption that varies periodically for varying the intensity of the X-ray radiation passed through the grating. This variation in intensity of the X-ray radiation causes the signal produced by the detector assembly to be amplitude modulated so that the frequency of the primary signal component is shifted from noise components of the signal caused by X-ray scatter contamination allowing the noise components to be filtered from the primary signal component so that scatter induced noise may be reduced or eliminated from the signal.

20 Claims, 10 Drawing Sheets

X-RAY SCATTER ELIMINATION BY FREQUENCY SHIFTING

BACKGROUND OF THE INVENTION

The present invention relates generally to radiographic imaging devices, particularly, computed tomography (CT) imaging devices, and the like, and more specifically, to apparatus and methods for separating noise caused by X-ray scatter contaminations from the primary signal of the detector of a radiographic imaging device so that the scatter may be reduced or eliminated from the signal, thereby allowing the image quality of the radiographic imaging device to be improved.

Single-row CT imaging devices or scanners, as well as CT imaging devices employing quasi-linear multi-row detectors, typically employ thin, straight metal collimators for eliminating scatter radiation. These metal collimators are oriented such that most of the scattered rays, which have their source at the scatter centers in the object being imaged (e.g., the body of a patient), intersect the collimator at oblique angles and are blocked. As a result, only rays approaching the detector directly from the direction of the radiation source pass through the collimator to the detector.

Cone-beam computed tomography (CBCT) imaging devices employ two-dimensional area detectors (typically referred to in the art as flat panels) in all cone beam imaging applications, be it conventional X-ray imaging or cone-beam computed tomography. CBCT imaging devices have typically been used for the reconstruction of high-contrast objects, such as bone or contrast filled vasculature. When used in such applications it is not necessary for the CBCT device to compensate for scatter radiation, since scatter induced noise is below the signal of interest. However, when used for soft tissue resolution, it becomes necessary to eliminate noise caused by scatter radiation to provide desired image quality.

To effectively block scatter radiation from the area detectors used by CBCT imaging devices using conventional technology, conically shaped collimators may be provided for each detection element of the area detector. Such collimators would be physically impractical to manufacture and maintain, especially in CBCT imaging devices employing megavolt (MV) sources, where the collimators would require substantial mass in order to block the high-energy photons created by the X-ray source. As a result, conventional metal collimators such as those used in single-row CT imaging devices are impractical to be used to block scatter radiation from the area detectors for CBCT imaging devices.

Consequently, it would be desirable to provide a method for separating the noise caused by X-ray scatter contaminations from the primary signal component of the signal produced by the detector of a radiographic imaging device so that the scatter induced noise in the signal may be reduced or eliminated without the use of metal collimators or like shielding devices.

SUMMARY OF THE INVENTION

Accordingly, the present invention is directed to apparatus and methods for separating and filtering noise caused by X-ray scatter contaminations from the primary signal component of the signal reaching the detector assembly of a radiographic imaging device so that scatter induced noise may be reduced or eliminated from the signal allowing the image quality of the radiographic imaging device to be improved. In exemplary embodiments, the present invention employs a scatter removal screen or grating disposed between the object being imaged and the detector assembly. The grating has an absorption coefficient that varies periodically for varying the intensity of the X-ray radiation passed through the grating. This variation in intensity of the X-ray radiation causes the signal produced by the detector assembly to be amplitude modulated so that the frequency of the primary signal component of the signal is shifted from noise components of the signal caused by X-ray scatter contamination allowing the noise components of the signal to be filtered from the primary signal component. In this manner, scatter induced noise may be reduced or eliminated without the use of metal collimators or like shielding devices.

It is to be understood that both the foregoing general description and the following detailed description are exemplary and explanatory only and are not necessarily restrictive of the invention claimed. The accompanying drawings, which are incorporated in and constitute a part of the specification, illustrate embodiments of the invention and together with the general description, serve to explain the principles of the invention.

DETAILED DESCRIPTION OF SPECIFIC EMBODIMENTS

Reference will now be made in detail to the presently preferred embodiments of the invention, examples of which are illustrated in the accompanying drawings.

Figure 1:
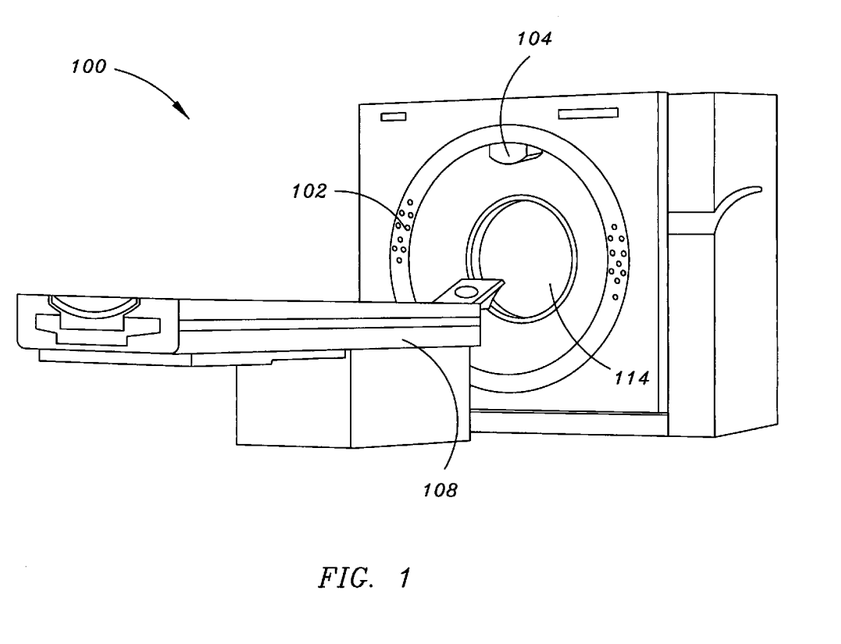
FIG. 1 is an isometric view illustrating a radiographic imaging device, specifically a CBCT imaging device, employing a scatter removal screen for providing X-ray scatter elimination via frequency shifting in accordance with an exemplary embodiment of the present invention.
Figure 2:
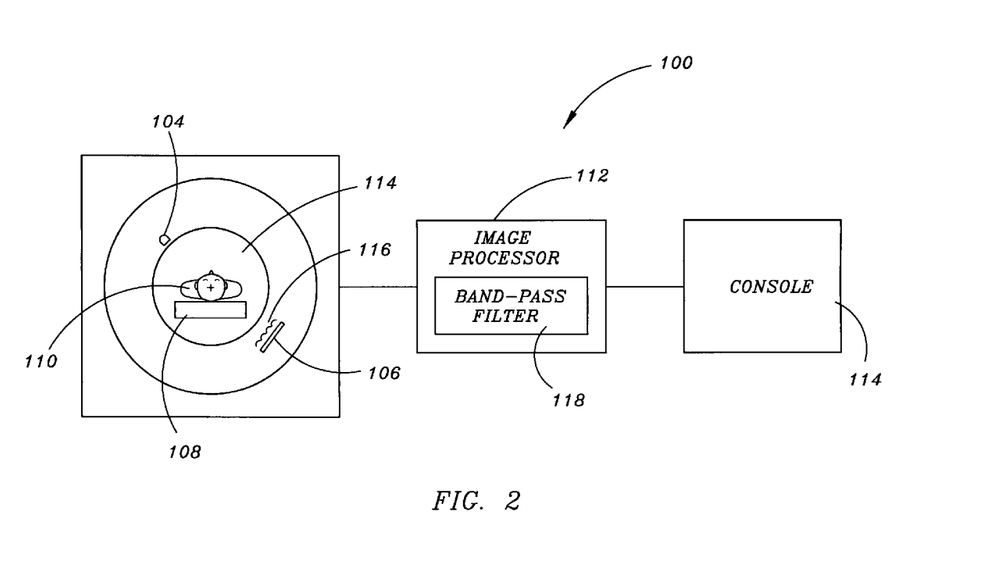
FIG. 2 is a block diagram further illustrating the CBCT imaging device shown in FIG. 1.

FIGS. 1 and 2 illustrate a radiographic imaging device 100 in accordance with an exemplary embodiment of the present invention. The radiographic imaging device 100 comprises a CBCT imaging device including a scanning unit or gantry 102 supporting an X-ray source 104 and a detector assembly 106, and a patient table 108 for supporting a patient 110 undergoing imaging. The X-ray source 104 emits X-ray radiation toward the body of a patient 110 lying on the patient table 108 so that at least part of the X-ray radiation passes through the body of the patient 110 to the detector assembly 106.

In exemplary embodiments, the radiographic imaging device 100 comprises a CBCT imaging device wherein the X-ray source 104 comprises a cone beam kV or MV source such as an X-ray tube, a linear accelerator assembly, or the like, while the detector assembly 106 comprises a two-dimensional area detector having a plurality of detection elements (e.g., ultra fast ceramic (UFC) detectors, charged coupled device (CCD) detectors, or the like) which convert incident X-rays of varying intensity to analog electrical signals. These analog signals are then amplified and converted to digital signals which are processed by the image processor 112 to produce an image comprising a plurality of pixels, each representing the intensity of the measured X-ray radiation incident on a detection element of the detector assembly 106.

In the embodiment shown, the gantry 102 comprises a ring shaped structure having an opening. The patient table 108 extends into this opening so that the body of the patent is placed between the X-ray source 104 and detector assembly 106. The X-ray source 104 and detector assembly 106 are then rotated within the gantry 102 about the patient table 108 allowing a transverse three-dimensional slice of the body of the patient 110 to be imaged from different angles. An image processing system 112 combines or reconstructs these separate images to provide a cross-sectional volumetric image of the slice. A console 114 provides a man-machine interface with the imaging device 100. For example, the console 114 may function as the control unit for controlling the imaging device 100 during examination procedures. The console 114 may further be used by physicians or technicians for evaluating the examination results.

Figure 3:
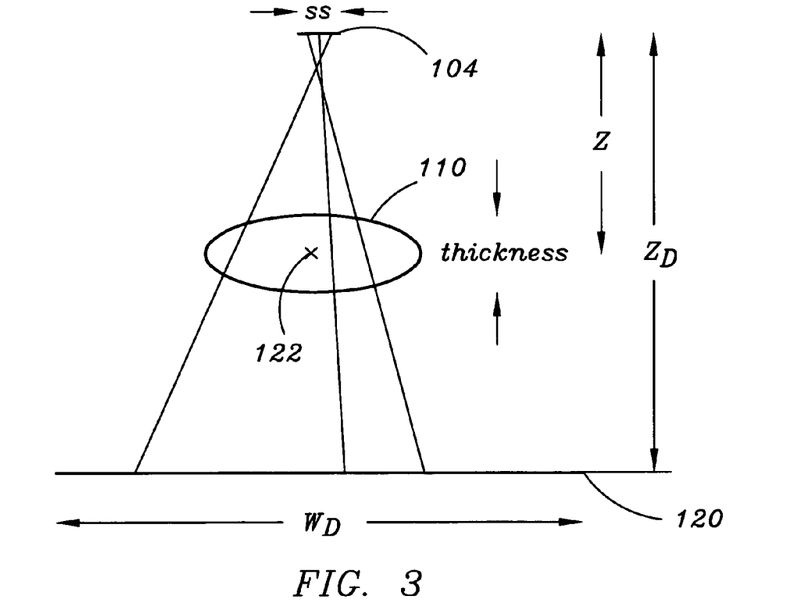
FIG. 3 is a diagrammatic view illustrating cone beam imaging by a CBCT imaging device such as the exemplary CBCT imaging device shown in FIG. 1.

FIG. 3 illustrates the geometry of cone beam imaging by a CBCT imaging device 100 shown in FIG. 1. As shown in FIG. 3, the X-ray source S 104 has a spot size ss, and is positioned at a distance $r_i$ from the isocenter of the gantry/patient table/patient arrangement. The detector assembly 106 is placed at a distance $r_D$ from the source 104 and has a width $w_D$. As described in the discussion of FIG. 1, the detector 120 is divided into a two-dimensional array of individual detection elements, each of which converts the X-rays incident upon its surface into electrical signals. The body of the patient 110, represented as an ellipse-shaped object with a given thickness for simplicity of illustration, is positioned within the imaging device 100 so that the isocenter of the arrangement falls within the body. In cone-beam CT imaging applications, the X-ray source and detector rotate together about the isocenter about an axis extending through the isocenter into the page.

As described in the discussion of FIG. 1, it is contemplated that the X-ray source 104 may be a kV source, as used in conventional X-ray imaging or computed tomography, or a MV source, such as the target of a clinical linear accelerator. With respect to the present invention, kV and MV sources 104 are discriminated primarily in terms of the spot size of the source 104 (which is significantly larger for MV beams) and the energy of the X-ray radiation. Further, as discussed in the description of FIG. 1, the radiographic imaging device 100 illustrated comprises a cone-beam CT (CBCT) imaging device, wherein the X-ray source 104 comprises a cone beam kV or MV source and the detector assembly 106 comprises a two-dimensional area detector. However, it is contemplated that the present invention may also be implemented in conventional CT imaging devices employing single row or quasi-linear multi-row detectors, and the like, without departing from the scope and spirit of the present invention.

The present invention separates noise caused by X-ray scatter contaminations from the primary signal component of the signal produced by the detector assembly 106 of the imaging device 100 in the Fourier domain so that scatter induced noise may be substantially reduced or eliminated from the useful signal. In this manner, the image quality of the imaging device 100 may be improved (e.g., by eliminating image artifacts, or the like). A carrier frequency is applied to the signal produced by the detector assembly 106 onto which the signal content is modulated. The carrier frequency is fixed for the primary portion of the signal corresponding to unscattered radiation coming from the source 104 and is a different frequency for all noise components of the signal caused by scattered radiation. It is noted that the noise components caused by the scattered radiation may have a range of carrier frequencies. Thus, the primary signal component generated from X-ray radiation emanating directly from the source 104 may be separated from noise components of the signal generated by scattered radiation via band-pass filtering, provided the carrier frequency of the primary signal component is sufficiently different from the carrier frequency of the closest component caused by scattered radiation.

As shown in FIG. 2, the present invention employs a screen or grating 116 disposed between the object 110 being imaged and the detector assembly 106 of the radiographic imaging device 100. The grating 116 has an absorption coefficient that varies periodically for periodically varying the intensity of the X-ray radiation passed through the grating 116. For example, in CBCT imaging device embodiments such as the embodiment illustrated, the grating 116 comprises a two-dimensional periodic pattern, having an absorption coefficient that varies periodically in two-dimensions (e.g., along the length and width of the detector), while in CT imaging device applications employing linear detectors, the grating 116 may comprise a one dimensional periodic pattern, having an absorption coefficient that varies periodically in one dimension (e.g., along the length of the detector). The variation in intensity of the X-ray radiation passed through the grating 116 causes the signal produced by the detector assembly 106 to be amplitude modulated so that the frequency of the primary signal component is shifted from the noise component of the signal allowing the noise component of the signal to be filtered from the primary signal component via a band-pass filter 118, or the like. In this manner, scatter induced noise in the signal may be reduced or eliminated without the use of metal collimators or like shielding devices.

Figure 4:
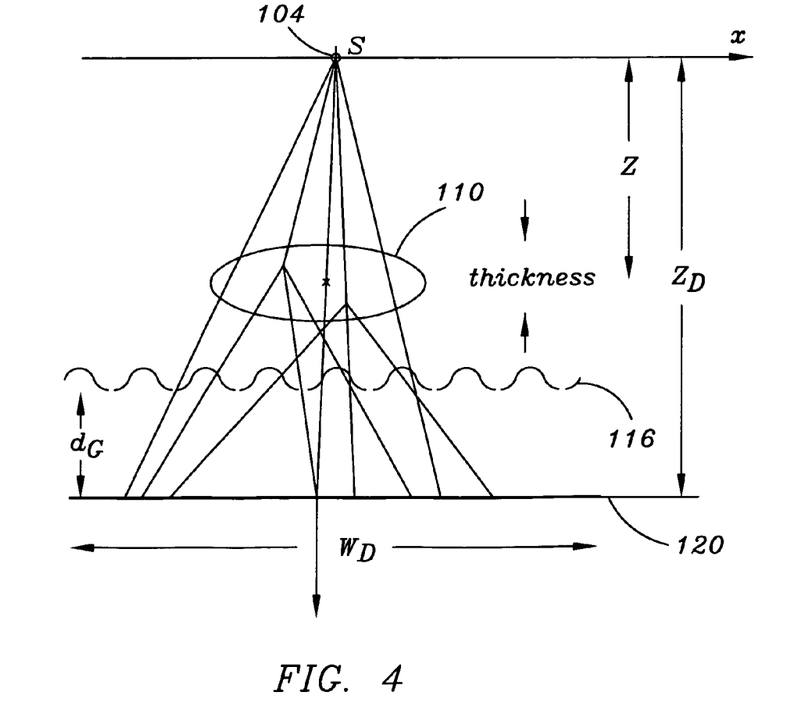
FIG. 4 is a diagrammatic view illustrating the cone beam imaging geometry shown in FIG. 3, augmented with a scatter removal screen in accordance with the present invention.

FIG. 4 illustrates the geometry shown in FIG. 3, augmented with the grating 116 shown in FIG. 2. Compared to the geometry of FIG. 3, the grating 116 introduces a layer (e.g., grating 116, FIG. 2) having an absorption coefficient that changes periodically as a function of position with respect to the surface (e.g., length and width) of the detector. The grating 116 is introduced at a distance $d_G$ from the detector 120. The periodic shape of the grating 116 multiplies the intensity of the X-ray radiation with a periodic signal along the detector direction. Thus, the content of the object (e.g., the body of a patient undergoing CT imaging) is amplitude modulated with a periodic function defined by the additional periodic grating 116.

Figure 5:
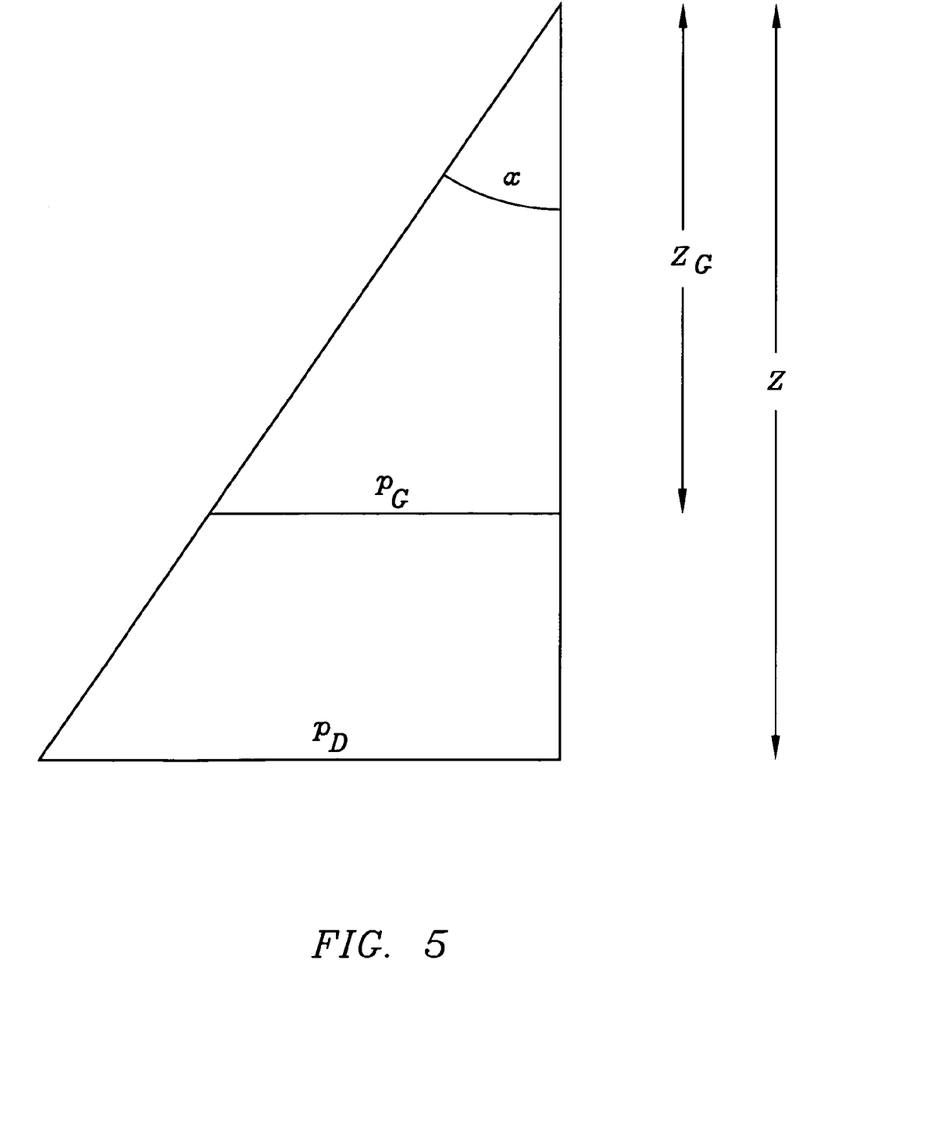
FIG. 5 is a diagrammatic view illustrating computation of the frequency of the screen grating at the detector.

For clarity of discussion, it is assumed that the spatial extension of the radiation source shrinks to zero (ss=0), and that the spatial frequency of the grating is therefore projected geometrically onto the detector. Further, it is assumed that the radiation source 104 is positioned at an arbitrary height z over the detector 120 of the detector assembly 106 (FIG. 2). Using the intercept theorem, the spatial frequency of the shadow that the grating 116 casts upon the detector 120 may be computed. First, the length of one period at the grating 116 is considered and compared to one shadow period at the detector 120 by the equation $$\frac{p_G}{p_D} = \frac{z_G}{z}, \qquad \text{EQN. 1}$$

where $$z_G = z - d_G \qquad \text{EQN. 2}$$

is the distance between the source and the grating, PG is the period of the grating 116 and $p_D$ is the shadow period at the detector 120. FIG. 5 illustrates this relationship.

The frequency is inversely proportional to the period of the signal. Thus, EQN. 1 may be inverted, giving $$\frac{f_G}{f_D} = \frac{z}{z_G} \qquad \text{EQN. 3}$$

where $f_G$ is the frequency of the grating 116 and $f_D$ is the frequency at the detector 120. EQN. 3 may then be combined with EQN. 2 and solved for the frequency at the detector $f_D$, as follows $$\frac{f_G}{f_D} = \frac{z}{z - d_G} \qquad \text{EQN. 4}$$

$$f_D = f_G \cdot \frac{z - d_G}{z}$$

for describing scatter reduction via amplitude modulation. The term $(z-d_G)/z$ is hereinafter referred to as the frequency shift factor $s_f$.

Figure 6:
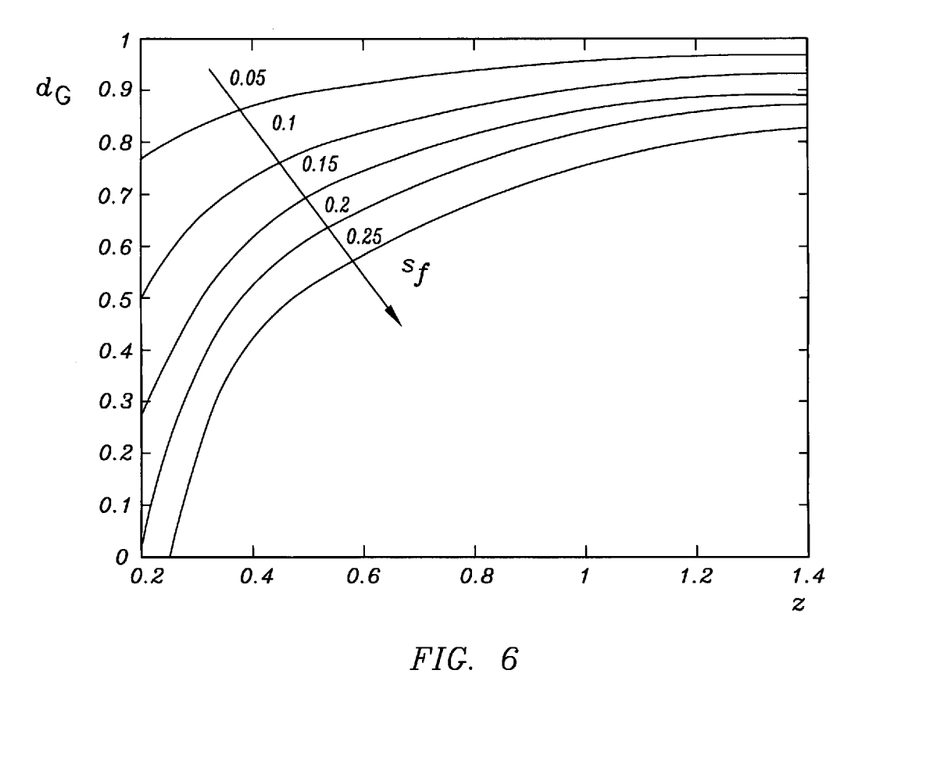
FIG. 6 is a graph illustrating the frequency shift factor ($s_f$) as a function of height of the scatter center above the detector (z) and the distance of the screen or grating above the surface of the detector ($d_G$)

In FIG. 6, the magnitude of the frequency shift factor $s_f$ is depicted as a function of height z of the radiation source 104 over the detector 120, with the distance $d_G$ from the detector 120 for exemplary value ranges of the height z of the radiation source 104 over the detector 120 and distance $d_G$ of the grating 116 from the detector 120. As the distance $d_G$ between the grating 116 and the detector 120 increases, the frequency at the detector 120 will differ for different values of height z of the radiation source 104 over the detector 120. The frequency $f_D$ will be highest when the height z assumes its maximum value $z_D$, i.e. when the origin of a ray of X-ray radiation is truly at the source of radiation S. However, every element that scatters radiation within the object will also act as an origin of a number of rays of X-ray radiation, since the Compton Effect will scatter rays from this center in random directions. These ray origins, however, will have a significantly smaller height above the detector z than $z_D$. As can be seen from EQN. 4 and FIG. 4, these smaller heights will lead to smaller effective frequencies of the shadows that the grating 116 will cast upon the detector 120.

Again using the intercept theorem, it can be seen that a periodic pattern at the grating 120 produces a periodic shadow with constant frequency at the detector 120 for arbitrary angles α not only for parallel projection but also for central projection. Thus, central projection also produces a strictly periodic shadow at the detector 120 when the grating 116 has a strictly periodic transmission coefficient.

Figure 7:
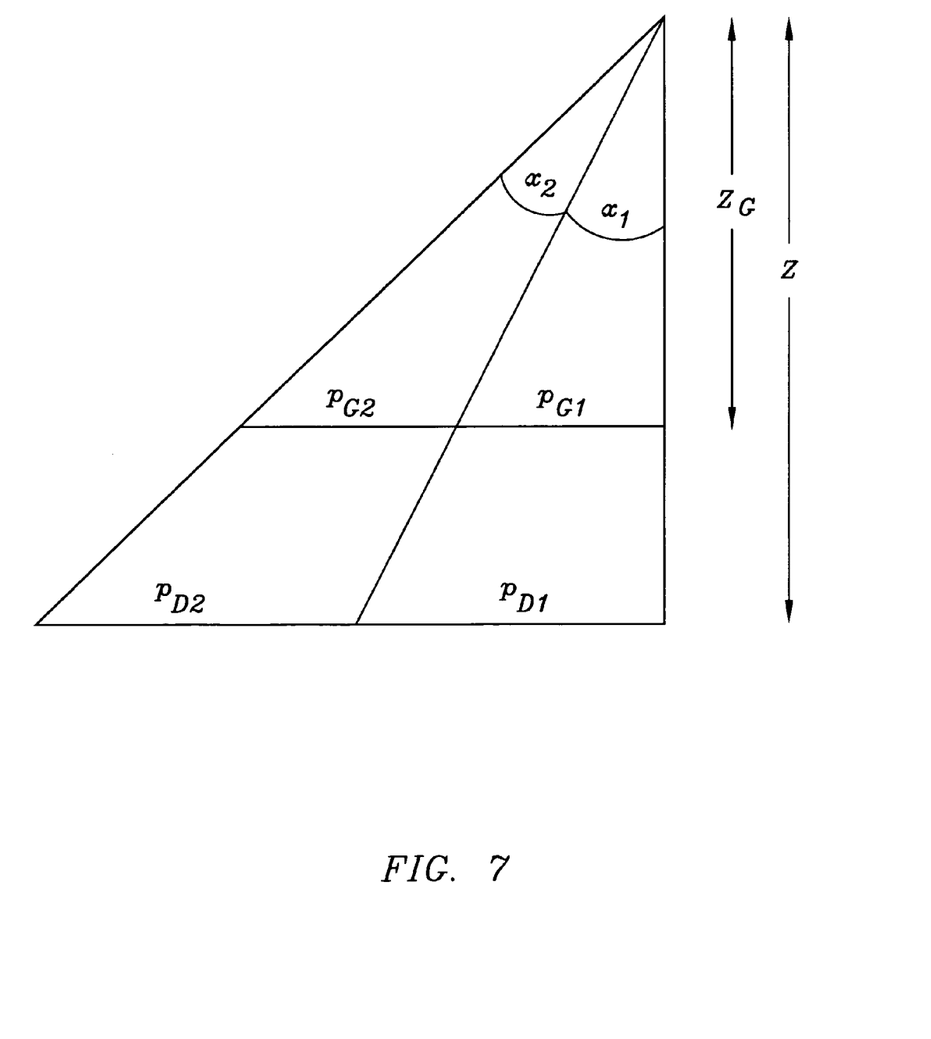
FIG. 7 is a diagrammatic view illustrating computation of the grating periodicity at the detector.

As shown in FIG. 7, periods $p_{B1}$ and $p_{B2}$ at the grating 116 and $p_{D1}$ and $p_{D2}$ at the detector 120 may be related using the intercept theorem $$\frac{z_G}{z} = \frac{p_{B1}}{p_{D1}}$$

$$= \frac{p_{B1} + p_{B2}}{p_{D1} + p_{D2}}$$

$$p_{D1} + p_{D2} = p_{D1} \cdot \frac{p_{B1} + p_{B2}}{p_{B1}}$$

$$p_{D2} = p_{D1} \cdot \left(\frac{p_{B1} + p_{B2}}{p_{B1}} - 1\right)$$

$$\frac{p_{D2}}{p_{D1}} = \frac{p_{B1} + p_{B2} - p_{B1}}{p_{B1}}$$

$$= \frac{p_{B2}}{p_{B1}}$$

For a periodic signal with periodicity $p_{B1}$ at the grating 116, $$p_{B2} = n \cdot p_{B1} \text{ with } n \in \{1,2,3,\ldots\}$$

so that $p_{B2}$ assumes in sequence the values of all period ends. Hence, $$p_{D2} = \frac{n \cdot p_{B1}}{p_{B1}} \qquad \text{EQN. 5}$$

$$p_{D2} = n \cdot p_{D1}.$$

Consequently, if all the values of $p_{B2}$-S of the grating are integer multiples of the first period $p_{B1}$, which is the case for a strictly periodic signal at the grating 116, then all the values of $p_{D2}$-S at the detector 120 are also the same integer multiples of period $p_{D1}$ at the detector 120. Thus, the X-ray radiation signal at the detector 120 is a strictly periodic signal and central projection generates a finite (since the detector 120 is finite) but otherwise strictly periodic carrier at the detector 120 with a frequency described by EQN. 4.

The frequency separation between this carrier, created from a radiation source at height $z=z_D$, and a carrier that is generated from a scatter center at height $z=z_i \pm z_p$, where $z_p$ is an arbitrary spot within the object 110, i.e. $0 \leq z_p \leq$ thickness/2 may now be determined. It is desirable to make this frequency separation sufficiently large to cleanly separate the noise component from the primary signal component in the Fourier domain. The frequency of a shadow that a scatter center at height z casts upon the detector 120 is the same, irrespective of where in x-direction over the detector that scatter center is. However, the phases of the periodic shadows differ for different values of x.

The frequency separation $\Delta f$ may be determined from EQN. 4 as $$\Delta f = f_G \cdot \left( \frac{z_D - d_G}{z_D} - \frac{z_D - z_i \mp z_p - d_G}{z_D - z_i \mp z_p} \right) \quad \text{EQN. 6}$$

$$= f_G \frac{(z_D - d_G)(z_D - z_i \mp z_p) - z_D(z_D - z_i \mp z_p - d_G)}{z_D(z_D - z_i \mp z_p)}$$

$$= f_G \frac{z_D(z_D - z_i \mp z_p + z_i \mp z_p - d_G) - d_G(z_D - z_i \mp z_p)}{z_D(z_D - z_i \mp z_p)}$$

$$= f_G \frac{d_G z_D - d_G(z_D - z_i \mp z_p)}{z_D(z_D - z_i \mp z_p)}$$

$$\Delta f = f_G d_G \frac{z_i \mp z_p}{z_D^2 - z_D(z_i \mp z_p)},$$

where $\Delta f$ is the frequency shift, $f_G$ is the frequency of the grating, $d_G$ is the distance between the grating and the detector assembly along an axis passing through the isocenter 122 of the radiographic imaging device 100, $z_i$ is the distance from the X-ray source 104 to the isocenter 122, $z_p$ is the distance from the isocenter 122 to a scatter center 124 within the object 110, and $z_D$ is the distance from the X-ray radiation source 104 to the detector 120 along an axis passing through the isocenter 122.

As can be seen from FIG. 4, the highest carrier frequency for scattered rays occurs for scatter points at the top of the object (e.g., the top of the body of the patient) 110. Thus, the minimum frequency separation $\Delta f_{min}$ may be determined from $$\Delta f_{min} = f_G d_G \frac{z_i - \frac{\text{thickness}}{2}}{z_D^2 - z_D\left(z_i - \frac{\text{thickness}}{2}\right)}. \quad \text{EQN. 7}$$

The third factor in EQN. 7 is determined by parameters of the radiographic imaging device 100 and object (e.g., patient) thickness, which are constant for a given setup. Hence, the minimum frequency separation $\Delta f_{min}$ may be described by the equation $$\Delta f_{min} = f_G d_G f_{machine}, \quad \text{EQN. 8}$$

where $$f_{machine} = \frac{z_i - \frac{\text{thickness}}{2}}{z_D^2 - z_D\left(z_i - \frac{\text{thickness}}{2}\right)}. \quad \text{EQN. 9}$$

The minimal separation of the two carriers, X-ray source generated and scatter center generated, is a linear function of the frequency $f_G$ of the grating 116 and the distance $d_G$ of the grating 116 from the detector 120 with a given machine constant $f_{machine}$ which may be determined for a given radiographic imaging device 100. For example, for a typical CBCT image device, with typical geometry parameters, $f_{machine}$ is approximately 1.104 1/m. Consequently, it is desirable to make both the frequency $f_G$ of the grating 116 and the distance $d_G$ of the grating 116 from the detector 120 as large as possible.

However, it will appreciated by those of skill in the art that, in practical radiographic imaging devices 100, the maximum distance $d_G$ of the grating 116 from the detector 120 is constrained by geometrical considerations, such as clearance around the patient 110 and patient table 108 (FIG. 1). Thus, it is desirable to determine the maximum achievable grating frequency $f_G$ for the imaging device 100. According to the Nyquist criteria, the maximum frequency $f_{Dmax}$ that can be sampled by a detector 120 having a given number of detection elements providing $s_D$ pixels over a given detector length $w_D$ is $$f_{Dmax} = \frac{1}{2} \cdot \frac{s_D}{w_D} \quad \text{EQN. 10}$$

which for a CBCT imaging device 100 of typical geometry is approximately 1280 1/m. Moreover, if it is assumed that the signal produced by the detector assembly 106 is a band limited signal (i.e. a smallest feature size $x_{pmin}$ to be imaged in an image at the isocenter 122 is assumed), an upper band limit frequency (of a "patient frequency") $f_{plim}$ may be determined from $$f_{plim} = \frac{1}{x_{pmin}}$$

Using EQN. 3 and substituting the distance from the X-ray radiation source 104 to the detector 120 $z_D$ for the distance z and the distance from the X-ray source 104 to the isocenter 122 $z_i$ for the distance $z_G$, the band limit frequency $f_{plim}$ projected onto the detector 120 may be determined from $$f_{Dlim} = f_{plim} \frac{z_i}{z_D}$$

$$= \frac{1}{x_{Pmin}} \frac{z_i}{z_D}$$

However, in amplitude modulation (AM), the carrier signal should be a frequency $f_{Dlim}$ below the band limit of the system. Thus, the maximum carrier frequency $f_{cmax}$ at the detector 120 is $$f_{c\,max} = f_{D\,max} - f_{D\,lim}$$

If this frequency $f_{cmax}$ is projected back to the grating 116, again using EQN. 3, and substituting the distance from the X-ray radiation source 104 to the detector 120 $z_D$ for the distance z, the following equation is obtained $$f_{Bmax} = f_{cmax} \frac{z_D}{z_G}$$

and using EQNS. 2, 9, and 10, the frequency projected to the grating 116 $f_{Bmax}$ may be determined from $$f_{Bmax} = (f_{Dmax} - f_{Dlim})\frac{z_D}{z_D - d_G} \quad \text{EQN. 11}$$

$$= \left(\frac{1}{2}\frac{s_D}{w_D} - \frac{1}{x_{Pmin}} - \frac{z_i}{z_D}\right)\frac{z_D}{z_D - d_G}$$

$$= \frac{s_D z_D}{2w_D(z_D - d_G)} - \frac{z_i}{x_{Pmin}(z_D - d_G)}$$

$$f_{Bmax} = \frac{1}{z_D - d_G}\left(\frac{s_D z_D}{2w_D} - \frac{z_i}{x_{Pmin}}\right)$$

Assuming that the finest structure that can be imaged by a CBCT imaging device at isocenter is about 2 mm in width, and using the geometry of typical CBCT imaging devices, the maximum carrier frequency $f_{Bmax}$ of the grating 116 may be related to the distance $d_G$ from the grating 116 to the detector 120 by $$f_{Bmax} = 1292/(1.4m - d_G).$$

Figure 8A:
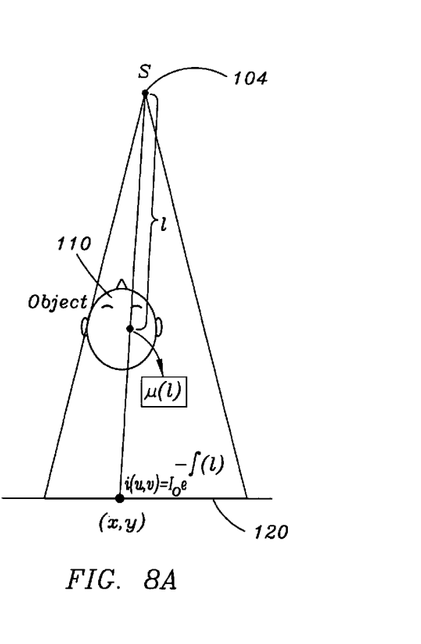
FIG. 8A is a diagrammatic view illustrating computation of the intensity of a ray of X-ray radiation reaching the detector from the source after passing through the object.
Figure 8B:
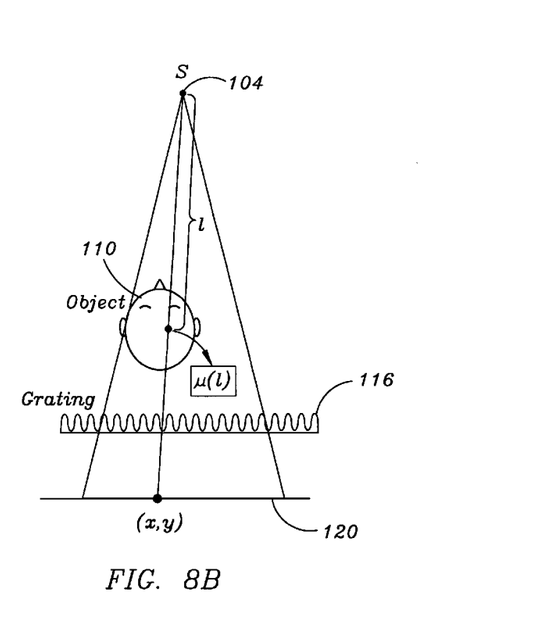
FIG. 8B is a diagrammatic view illustrating computation of the intensity of a ray of X-ray radiation reaching the detector from the source after passing through the object and a grating in accordance with the present invention.

FIGS. 8A and 8B illustrates computation of the intensity of a ray of X-ray radiation reaching the detector from the source after passing through the object, both without a grating (FIG. 8A) and with a grating (FIG. 8B). The intensity of a ray of X-ray radiation reaching a detector 120 is expressed by $$i(x,y) = I_0 \, e^{-\int \mu(l) dl},$$

where (x, y) is a point on the detector 120, $I_0$ is the intensity of the X-ray reaching the detector 120 traversing the distance from the source 104 to the detector 120 entirely through air or a vacuum, $\mu(l)$ represents the absorption coefficient of the material along a ray emanating from the source 104 to the detector 120 at the point (x, y) at the distance l from the source 104.

Figure 9:
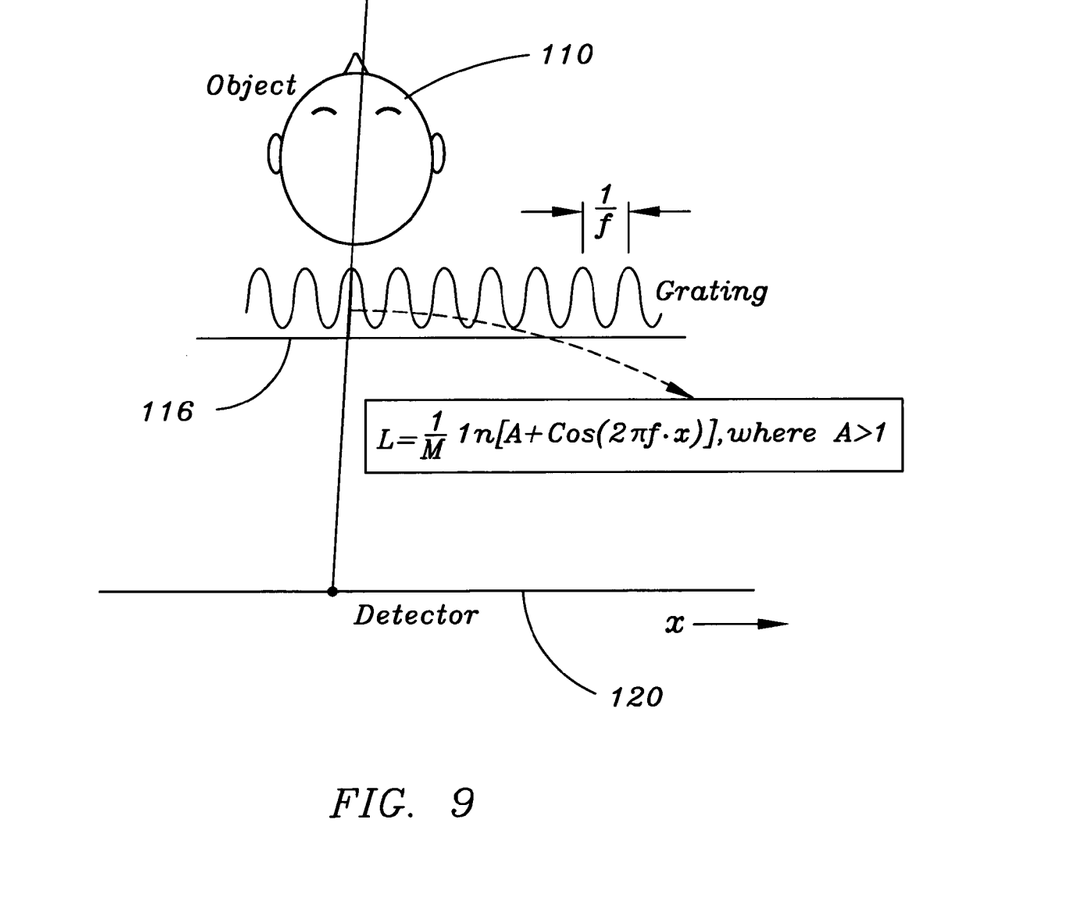
FIG. 9 is a diagrammatic view illustrating an exemplary grating that results in a pure shift of the primary X-ray signal component.

FIG. 9 illustrates an exemplary grating 116 that results in a pure shift of the primary X-ray signal component in accordance with an exemplary embodiment of the invention. In the embodiment for the grating illustrated in FIG. 9, the grating 116 is made from a material having a constant X-ray absorption coefficient M. Exemplary materials from which the grating may be made include, but are not limited to copper or lead. The shape of the grating 116 is such that a ray emanating from the source S 104 passing through the grating 116 will have a length L determined by $$L = \frac{1}{M}\ln[A + \cos(2\pi f \cdot x)],$$

where f is the spatial frequency of the grating 116 along a dimension x of the detector 120 and A is a constant greater than 1.

The intensity of the ray of X-ray radiation at the detector 120 is a combination of the intensity resulted from the X-ray radiation absorbed by the object 110 and the X-ray radiation absorbed by the grating 116. The intensity i is described by:

$$i = I_0 e^{-\{\int \mu_0 dl + M\{\frac{1}{M}\ln[A + \cos(2\pi f \cdot x)]\}\}} \quad \text{EQN. 12}$$

$$i = I_0 e^{-\int \mu_0 dl} \cdot e^{-M\{\frac{1}{M}\ln[A + \cos(2\pi f \cdot x)]\}}$$

-continued $$i = i_o \cdot e^{-\ln[A + \cos(2\pi f \cdot x)]}$$

$$i = i_o \cdot [A + \cos(2\pi f \cdot x)] = A \cdot i_o + A \cdot i_o \cdot \cos(2\pi f \cdot x).$$

Figure 10:
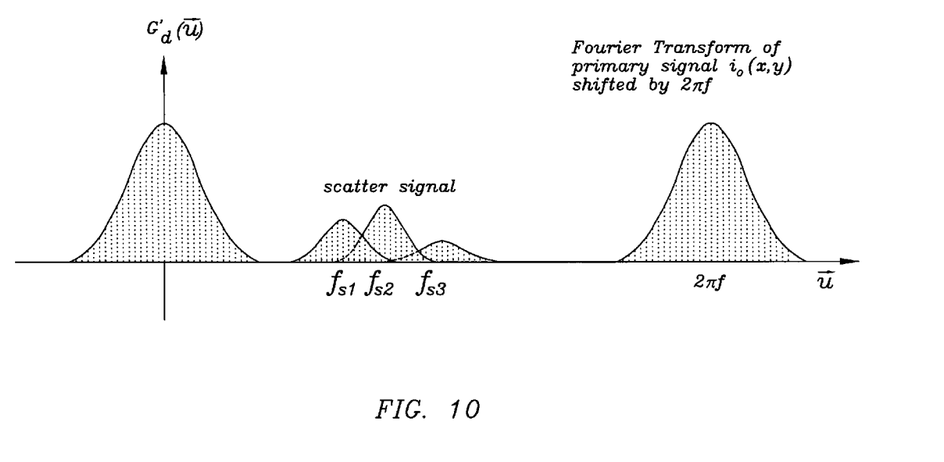
FIG. 10 is a graph illustrating a Fourier transform of the intensity at the detector, depicting the shift of the primary X-ray signal component from components caused by scatter contamination.

Thus, as described by EQN. 12, the intensity of the primary X-ray signal component is multiplied by a Cosine function. This multiplication results in a frequency shift of $2\pi \cdot f$ in the frequency domain. This frequency shift may then be used to filter the primary signal component from scatter signals. FIG. 10 illustrates a Fourier transform of the intensity at the detector 120, depicting the shift of the primary signal component by $2\pi \cdot f$ thereby separating the primary signal component from noise components caused by scatter contamination (e.g., $f_{s1}$, $f_{s2}$ and $f_{s3}$).

Figure 11:
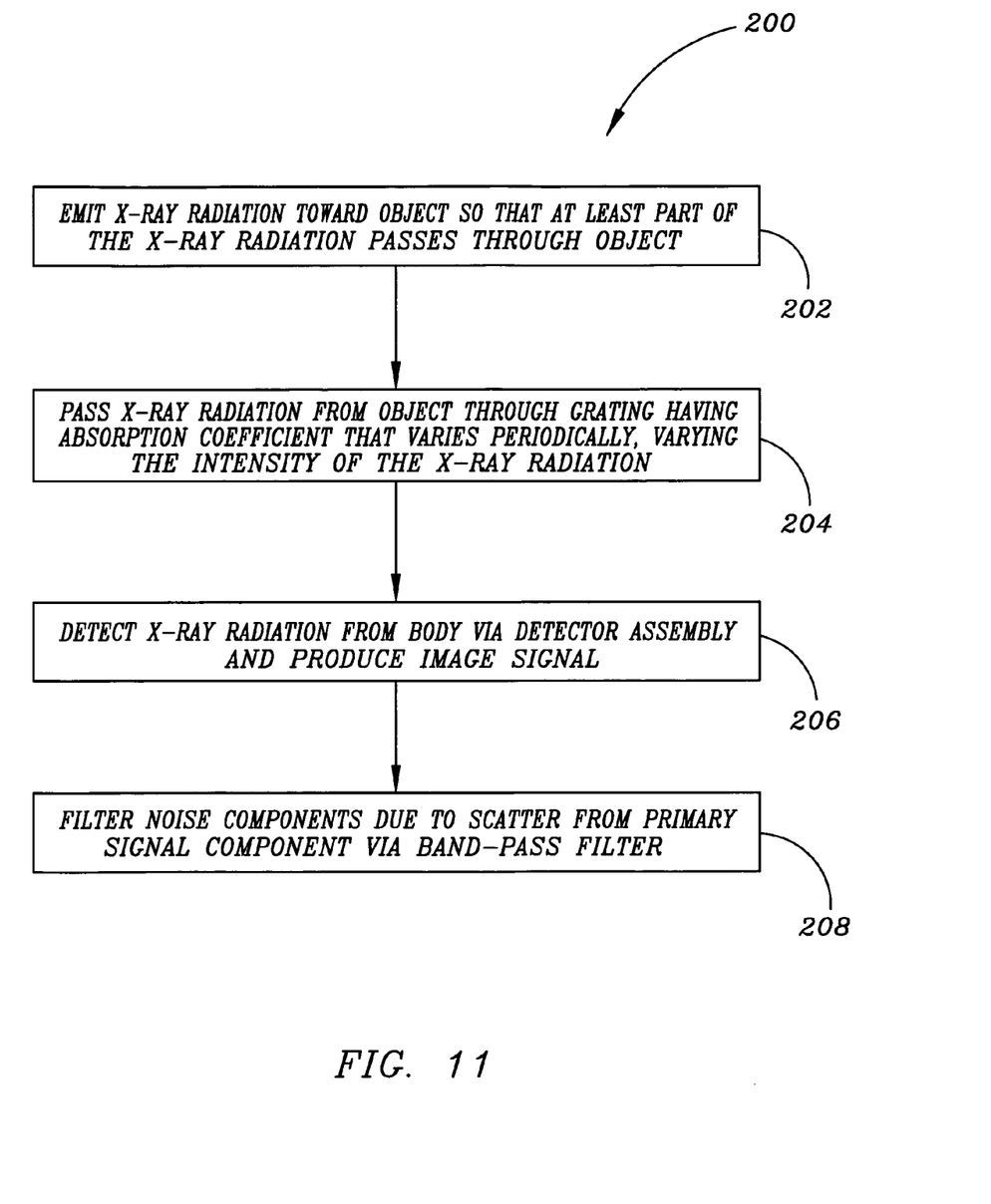
FIG. 11 is a flow diagram illustrating a method for removing noise components caused by X-ray scatter contamination from the primary signal component of the signal produced by the detector assembly of the CBCT imaging device in accordance with an exemplary embodiment of the present invention.

FIG. 11 illustrates an exemplary method 200 suitable for use by the radiographic imaging device 100, for removing noise components caused by X-ray scatter contamination from the primary signal component of the signal produced by the detector assembly 106 in accordance with an exemplary embodiment of the present invention. As described in the discussion of FIGS. 1 through 3, the X-ray source 104 emits X-ray radiation toward an object such as the body of the patient undergoing CT imaging so that at least part of the X-ray radiation passes through the object, at step 202. The X-ray radiation from the object is then passed through the grating 116, at step 204, varying the intensity of the X-ray radiation passing through the grating 116 in a periodic manner. The detector assembly 106 receives the X-ray radiation passed through the object 110, at step 206, and produces a signal in response thereto that includes a primary signal component and a noise component from X-ray scatter contamination. As discussed, the variation in intensity of the X-ray radiation passed through the grating causes a shift of the frequency of the primary signal component from the frequency of the noise component as described in the discussion of FIGS. 4 through 7, allowing the signal to be filtered, at step 208, by frequency, by passing the signal through a band-pass filter, or the like, for separating the noise component from the primary signal component.

Although the invention has been described with a certain degree of particularity, it should be recognized that the elements thereof may be altered by persons skilled in the art without departing from the scope and intent of the invention. In the exemplary embodiments, the method 200 illustrated in FIG. 11 may be implemented as sets of instructions or software readable by components of the radiographic imaging device 100 shown in FIG. 2 (e.g., the image processor 112, the console 114, or the like). It is understood that the specific order or hierarchy of steps in the method 200 is an example of an exemplary approach. Based upon design preferences, it is contemplated that the specific order or hierarchy of steps in the method 200 can be rearranged or modified while remaining within the scope of the present invention. The accompanying method claims present elements of the various steps of the method 200 in a sample order, and are not meant to be limited to the specific order or hierarchy presented.

It is believed that the present invention and many of its attendant advantages will be understood by the foregoing description, and it will be apparent that various changes may be made in the form, construction and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. An apparatus for eliminating noise caused by X-ray scatter contamination in a radiographic imaging device having an X-ray source for emitting a beam of X-ray radiation toward an object, a detector assembly for receiving at least part of the X-ray radiation after the X-ray radiation passes through the object and producing a signal in response thereto, the signal including a primary signal component and a noise component caused by X-ray scatter contamination, comprising:

a grating disposed between the object and the detector assembly, the grating having an absorption that varies periodically for varying and amplitude modulating the intensity of the X-ray radiation passed through the grating and received by the detector assembly;

a band-pass filter for filtering the noise component of the signal from the primary signal component, wherein the variation in intensity of the X-ray radiation passed through the grating causes a frequency shift of the primary signal component from the noise component of the signal for filtering the noise component of the signal from the primary signal component.

2. The apparatus as claimed in claim 1, wherein the variation in intensity of the X-ray radiation passed through the grating causes a frequency shift of $2\pi \cdot f$ in the primary signal component in the frequency domain, where f is the spatial frequency of the grating.

3. The apparatus as claimed in claim 1, wherein the variation in intensity of the X-ray radiation passed through the grating causes amplitude modulation of the signal resulting in the frequency shift.

4. The screen as claimed in claim 1, wherein the frequency shift of the primary signal component of the signal produced by the detector assembly from the noise component of the signal produced by the detector assembly is described in two dimensions by $$\Delta f = f_G d_G \frac{z_i \pm z_p}{z_D^2 - z_D(z_i \pm z_p)}$$

where $\Delta f$ is the frequency shift, $f_G$ is the frequency of the grating, $d_G$ is the distance between the grating and the detector assembly along an axis passing through the isocenter of the radiographic imaging device, $z_i$ is distance from the X-ray source to the isocenter, $z_p$ is the distance from the isocenter to a scatter center within the object, and $z_D$ is the distance from the X-ray radiation source to the detector assembly along an axis passing through the isocenter.

5. The screen as claimed in claim 4, wherein the frequency shift of the primary signal component of the signal produced by the detector assembly from the noise component of the signal produced by the detector assembly has a minimum value, the minimum frequency shift being described in two dimensions by $$\Delta f_{min} = f_G d_G \cdot f_{machine}$$

where $\Delta f_{min}$ is the minimum frequency shift and $f_{machine}$ is a constant described by $$f_{machine} = \frac{z_i - \frac{thickness}{2}}{z_D^2 - z_D\left(z_i - \frac{thickness}{2}\right)}$$

where thickness is the thickness of the object.

6. The apparatus as claimed in claim 1, wherein the X-ray source comprises a cone-beam source, the detector assembly comprises a two-dimensional area detector, and the absorption varies periodically in two dimensions.

7. A radiographic imaging device, comprising:

an X-ray source for emitting a beam of X-ray radiation toward an object;

a detector assembly for receiving at least part of the X-ray radiation after the X-ray radiation passes through the object and producing a signal in response thereto, the signal including a primary signal component and a noise component caused by X-ray scatter contamination; and a grating disposed between the object and the detector assembly, the grating having an absorption that varies periodically for varying the intensity of X-ray radiation received by the detector assembly, wherein the variation in intensity of the X-ray radiation passed through the grating causes a frequency shift of the primary signal component from the noise component of the signal for filtering the noise component of the signal from the primary signal component.

8. The radiographic imaging device as claimed in claim 7, further comprising an image processor for filtering the noise component of the signal from the primary signal component.

9. The radiographic imaging device as claimed in claim 8, wherein the image processor comprises a band-pass filter for filtering the noise component from the primary signal component.

10. The radiographic imaging device as claimed in claim 7, wherein the variation in intensity of the X-ray radiation passed through the grating causes a frequency shift of $2\pi \cdot f$ in the primary signal component in the frequency domain, where f is the spatial frequency of the grating.

11. The radiographic imaging device as claimed in claim 7, wherein the X-ray source comprises a cone-beam source and the detector assembly comprises a two-dimensional area detector.

12. The radiographic imaging device as claimed in claim 7, wherein the variation in intensity of the X-ray radiation passed through the grating causes amplitude modulation of the signal resulting in the frequency shift.

13. The radiographic imaging device as claimed in claim 7, wherein the frequency shift of the primary signal component of the signal produced by the detector assembly from the noise component of the signal produced by the detector assembly is described in two dimensions by $$\Delta f = f_G d_G \frac{z_i \pm z_p}{z_D^2 - z_D(z_i \pm z_p)}$$

where $\Delta f$ is the frequency shift, $f_G$ is the frequency of the grating, $d_G$ is the distance between the grating and the detector assembly along an axis passing through the isocenter of the radiographic imaging device, $z_i$ is distance from the X-ray source to the isocenter, $z_p$ is the distance from the isocenter to a scatter center within the object, and $z_D$ is the distance from the X-ray radiation source to the detector assembly along an axis passing through the isocenter.

14. The radiographic imaging device as claimed in claim 13, wherein the frequency shift of the primary signal component of the signal produced by the detector assembly from the noise component of the signal produced by the detector assembly has a minimum value, the minimum frequency shift being described in two dimensions by $$\Delta f_{min} = f_G d_G \cdot f_{machine}$$

where $\Delta f_{min}$ is the minimum frequency shift and $f_{machine}$ is a constant described by $$f_{machine} = \frac{z_i - \frac{thickness}{2}}{z_D^2 - z_D\left(z_i - \frac{thickness}{2}\right)}$$

where thickness is the thickness of the object.

15. A method for eliminating noise caused by X-ray scatter contamination in a radiographic imaging device, comprising:
  emitting X-ray radiation toward an object so that at least part of the X-ray radiation passes through the object;
  passing at least part of the X-ray radiation from the object through a grating having an absorption coefficient that varies periodically for varying the intensity of the X-ray radiation passing through the grating;
  detecting at least part of the X-ray radiation passed through the object and the grating and producing a signal in response thereto, the signal including a primary signal component and a noise component from X-ray scatter contamination, wherein the variation in intensity of the X-ray radiation passed through the grating causes a shift of the frequency of the primary signal component from the frequency of the noise component; and
  filtering the signal by frequency for separating the noise component from the primary signal component.

16. The method as claimed in claim 15, wherein the step of filtering the signal comprises passing the signal through a band-pass filter.

17. The method as claimed in claim 15, wherein the variation in intensity of the X-ray radiation passed through the grating causes a frequency shift of $2\pi \cdot f$ in the primary signal component in the frequency domain, where f is the spatial frequency of the grating.

18. The method as claimed in claim 15, wherein the variation in intensity of the X-ray radiation passed through the grating causes amplitude modulation of the signal resulting in the frequency shift.

19. The method as claimed in claim 15, wherein the frequency shift of the primary signal component of the signal produced by the detector assembly from the noise component of the signal produced by the detector assembly is described in two dimensions by $$\Delta f = f_G d_G \frac{z_i \pm z_p}{z_D^2 - z_D(z_i \pm z_p)}$$

where $\Delta f$ is the frequency shift, $f_G$ is the frequency of the grating, $d_G$ is the distance between the grating and the detector assembly along an axis passing through the isocenter of the radiographic imaging device, $z_i$ is distance from the X-ray source to the isocenter, $z_p$ is the distance from the isocenter to a scatter center within the object, and $z_D$ is the distance from the X-ray radiation source to the detector assembly along an axis passing through the isocenter.

20. The method as claimed in claim 19, wherein the frequency shift of the primary signal component of the signal produced by the detector assembly from the noise component of the signal produced by the detector assembly has a minimum value, the minimum frequency shift being described in two dimensions by $$\Delta f_{min} = f_G d_G \cdot f_{machine}$$

where $\Delta f_{min}$ is the minimum frequency shift and $f_{machine}$ is a constant described by $$f_{machine} = \frac{z_i - \frac{thickness}{2}}{z_D^2 - z_D\left(z_i - \frac{thickness}{2}\right)}$$

where thickness is the thickness of the object.

* * * * *